(12) United States Patent
Green

(10) Patent No.: US 6,471,708 B2
(45) Date of Patent: Oct. 29, 2002

(54) INTRAOCULAR LENS AND ADDITIVE PACKAGING SYSTEM

(75) Inventor: George F. Green, St. Louis, MO (US)

(73) Assignee: Bausch & Lomb Incorporated, Rochester, NY (US)

(*) Notice: Subject to any disclaimer, the term of this patent is extended or adjusted under 35 U.S.C. 154(b) by 45 days.

(21) Appl. No.: 09/746,451

(22) Filed: Dec. 21, 2000

(65) Prior Publication Data

US 2002/0082609 A1 Jun. 27, 2002

(51) Int. Cl.7 .................................................. A61F 9/007
(52) U.S. Cl. ........................................ 606/107; 623/6.12
(58) Field of Search ................................ 606/107, 108; 623/6.12

(56) References Cited

U.S. PATENT DOCUMENTS

| | | | |
|---|---|---|---|
| 4,257,521 A | 3/1981 | Poler | 206/5.1 |
| 4,326,306 A | 4/1982 | Poler | 3/13 |
| 4,423,809 A | 1/1984 | Mazzocco | 206/5.1 |
| 4,697,697 A | 10/1987 | Graham et al. | 206/5.1 |
| 4,844,242 A | 7/1989 | Chen et al. | 206/5.1 |
| 5,281,227 A | 1/1994 | Sussman | 606/107 |
| 5,290,293 A | 3/1994 | Van Noy et al. | 606/107 |
| 5,454,818 A | 10/1995 | Hambleton et al. | 606/107 |
| 5,607,433 A | 3/1997 | Polla et al. | 606/107 |
| 5,944,725 A * | 8/1999 | Cicenas et al. | 606/107 |
| 5,947,975 A * | 9/1999 | Kikuchi et al. | 606/107 |

* cited by examiner

Primary Examiner—Michael H. Thaler
(74) Attorney, Agent, or Firm—Katherine McGuire

(57) ABSTRACT

A packaging system for an intraocular lens and optionally an additive material that can be used to insert a packaged intraocular lens into an eye through a relatively small incision. Methods for inserting an intraocular lens into an eye using such packaging system are within the scope of the present invention.

23 Claims, 5 Drawing Sheets

INTRAOCULAR LENS AND ADDITIVE PACKAGING SYSTEM

FIELD OF THE INVENTION

The present invention relates to an intraocular lens packaging system with an optional additive reservoir and a method of making and using the same. More particularly, the present invention relates to a packaging system that may be used to store an intraocular lens and optionally an additive material, such as a lubricant, until use during an ophthalmic surgical procedure at which time the packaging system may be used as an intraocular lens inserter.

BACKGROUND OF THE INVENTION

The natural crystalline lens of the eye plays a primary role in focusing light onto the retina for proper vision. However, vision through the natural lens may become impaired due to an injury or the formation of a cataract caused by aging or disease. To restore vision in the case of a cataractous lens, the natural lens is typically removed and replaced with an artificial lens. Implantation of an artificial lens may also be useful to make a refractive correction in an eye without the removal of a non-cataractous natural crystalline lens.

Many surgical procedures have been developed for removing the natural lens if cataractous. Typically, a slender implement is inserted through a small incision in the eye to contact the natural lens. The implement includes a cutting edge that is ultrasonically vibrated to emulsify the lens. The emulsified fragments of the lens are then aspirated out of the eye through a passage located in the proximity of the cutting edge. The slender nature of the implement enables extraction of the lens through a small incision in the eye. Removal of the natural lens through a relatively small incision is preferred over other procedures requiring larger incisions. Procedures requiring a relatively smaller incision can lessen the trauma and complications experienced both during surgery and postoperatively.

Because the incision required to remove a natural lens is relatively small, artificial intraocular lenses that do not require any enlargement of the surgical incision for implantation are preferred. Intraocular lenses commonly include a generally disk shaped optic which focuses light on the retina and at least one outwardly extending haptic portion for proper positioning and support of the optic within the eye. Flexible intraocular lenses enable a lens to be folded and compressed so as to occupy a smaller cross-sectional area for passage of the lens through a relatively small surgical incision in an aphakic eye, wherein the natural lens has been removed, or a phakic eye, wherein the natural lens has not been removed. Once inserted through the narrow incision, the intraocular lens is permitted to expand to its original size and shape.

A number of devices have been developed to insert a flexible intraocular lens through a relatively small incision in a phakic or aphakic eye. For example, in U.S. Pat. No. 4,681,102 a hinged cartridge which closes about a lens to fold the lens into a narrower configuration is disclosed. The cartridge is placed into an inserter mechanism that advances the folded lens into the eye. The inserter, however, requires several components to be manipulated and assembled to accomplish the folding and implantation procedure. Rheinish et al. disclose in U.S. Pat. No. 5,275,604, a device whereby a lens is pushed through a narrowing lumen formed with spiraling grooves to fold a lens into a smaller size as it is moved toward an eye for implantation therein. The manufacture of spiraling grooves in a tapering lumen is difficult if not impossible to accomplish in a practical manner. In U.S. Pat. No. 5,304,182, Rheinish et al. disclose a device whereby a curling member is shifted laterally to fold a lens into a size small enough to pass through a narrow incision. However, no locking arrangement is provided to ensure complete closing of the curling member which may cause complications.

Moreover, while the devices disclosed in the noted patents function to reduce the cross-sectional size of a lens for insertion into an eye, each requires opposing side edges of the lens to be folded over on themselves in order to fit through a narrow incision. As a result, the lens must unfold within the eye to regain its original shape and size. Such unfolding requires the lens, and particularly the haptic, to be swung in an arc, thus risking damage to the interior of the eye. Additionally, the folding and pressing of the lens required to pass the lens through a small incision places a significant amount of inward pressure on the lens. As a result, the lens is frequently discharged from the inserter with considerable force and velocity. This forceful, uncontrolled release of the lens within the eye also places the interior of the eye at risk of being injured.

Further, many known inserters do not maintain control of the orientation of the lens as the lens is advanced into the eye. Consequently, the lens may rotate or turn about a longitudinal axis as it is pushed through the inserter. Most lenses, however, are made to be set within the eye in a specific orientation. Accordingly, such turning of the lens can result in the lens being placed in the eye with improper orientation.

In addition to the difficulties noted above associated with using known intraocular lens inserters, difficulties also arise with regard to properly loading the intraocular lens within the inserter. If an intraocular lens is loaded within an inserter improperly, the lens could possibly be implanted within the eye with improper orientation or the lens could be damaged or destroyed. Often times, if not always, when loading an intraocular lens within an inserter, a viscoelastic or similar lubricating material is necessary to avoid damage to the lens as the lens is forced through the inserter. A viscoelastic or lubricating material is loaded within the inserter upon loading the lens to ease insertion and lessen the possibility of lens damage. However, the additional step of loading a viscoelastic or lubricating material at the time of loading the intraocular lens is at times cumbersome and inconvenient.

Accordingly, a long felt need exists for a simple, reliable, cost effective and convenient device and method of using the same to implant an intraocular lens within an eye while minimizing potential injury to the eye.

SUMMARY OF THE INVENTION

The present invention pertains to an intraocular lens packaging system with an optional additive material reservoir, and a method of making and using the same to implant an intraocular lens (IOL) within an eye in a simple, reliable, cost effective and convenient manner. The packaging system of the present invention in its preferred construction provides a non-permanently sealed additive material reservoir for packaging an additive material such as a viscoelastic material, a lubricant, an anti-inflammatory agent, an antibiotic or a combination thereof and a non-permanently sealed IOL compression chamber for packaging a loaded, properly oriented IOL. In using the subject packaging system, both the IOL compression chamber seal and the optional additive material reservoir seal, which are preferably one in the same, are removed. Upon removal of the seal(s), additive material is discharged from the additive material reservoir into the IOL compression chamber just prior to compression of the IOL. Upon compression, the IOL is laterally compressed into a smaller cross-sectional configuration for insertion through a relatively small incision in the eye. Since the side edges of the lens are not folded over on themselves during lateral compression, the IOL does not swing open within the eye in order to regain its original shape. As a result, the risk of a part of the IOL striking and injuring an interior portion of the eye after release of the lens from the inserter is reduced.

Accordingly, it is an object of the present invention to provide a packaging system for an intraocular lens that may be used as an inserter.

Another object of the present invention is to provide a packaging system for both an additive material and an intraocular lens.

Another object of the present invention is to provide a packaging system for both an additive material and an intraocular lens that may be used as an inserter.

Another object of the present invention is to provide a packaging system that may be used to implant an intraocular lens within an eye with reduced risk of injuring internal portions of the eye.

Another object of the present invention is to provide a packaging system that is relatively simple and convenient to use in a surgical procedure.

Still another object of the present invention is to provide an additive material and intraocular lens packaging system that is reliable and cost effective.

These and other objectives and advantages of the present invention, some of which are specifically described and others that are not, will become apparent from the detailed description, examples and claims that follow.

DETAILED DESCRIPTION OF THE INVENTION

Figure 1:
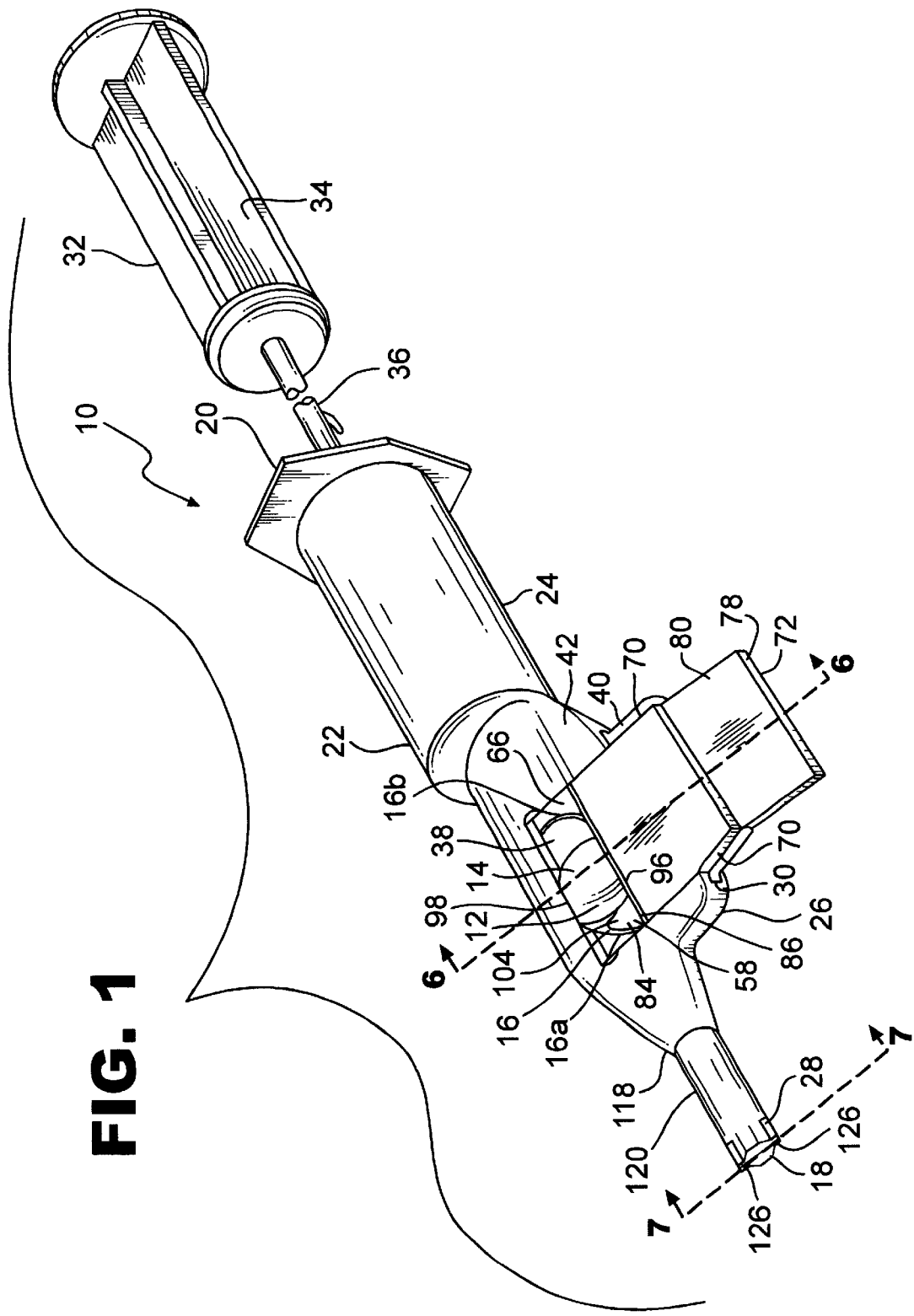
FIG. 1 is a perspective view of an intraocular lens and additive material packaging system in accordance with the present invention.

The present invention pertains to a packaging system 10 as illustrated in FIGS. 1 through 7. Packaging system 10 is used to package an intraocular lens (IOL) 12 and optionally an additive material 13. Packaging system 10 may also be used as an inserter for implanting IOL 12 within a phakic or an aphakic eye. IOL 12 typically includes an optic portion 14 and one or more haptic elements 16. Haptic elements 16 have one of any number of forms, but most commonly have a plate or loop form. For purposes of illustration and not limitation, the use of packaging system 10 is described herein with an IOL 12 having looped haptic elements 16.

In the preferred construction, packaging system 10 includes a tubular member 22 for receiving and directing IOL 12 into an eye through a relatively small incision of approximately 3.5 mm or less. Tubular member 22 generally includes a body portion 24, a compression chamber 26, a cannula 28 and an open passage 18 extending axially throughout the length of tubular member 22. Body portion 24, compression chamber 26 and cannula 28 are preferably formed as a unitary molded member from a material suitable therefor. However, an integral assembly of plural parts from a variety of suitable materials could also be used.

Proximal open end 20 of tubular member 22 is in fluid communication with open passage 18 and adapted to receive a plunger 32. Plunger 32 includes a base 34 matingly received in body portion 24 and a tip 36 which extends from base 34 within body portion 24. Upon further movement of base 34 within body portion 24, tip 36 engages and pushes IOL 12 through cannula 28 and into an eye. Base 34 of plunger 32 is shaped to prevent rotation of plunger 32 relative to tubular member 22. For example, base 34 and open passage 18 may have complimentary non-circular shapes or a key and keyway construction. While plunger 32 is preferably advanced manually into open passage 18 of body portion 24, alternatively, a motor or other driving arrangement could be used to move plunger 32.

Compression chamber 26 includes an opening 38 in fluid communication with open passage 18 for receiving, compressing and directing IOL 12 into cannula 28. Compression chamber 26 includes a support 30 molded between body portion 24 and cannula 28, and a compressor 40 which is mounted for movement within support 30. Support 30 includes an extended wing portion 42 having a base portion 44 and a pair of alignment arms 46. Alignment arms 46 and base 44 collectively define a channel 48 into which compressor 40 is moveably received. A lip 50 is formed on each alignment arm 46 opposite base 44 to maintain compressor 40 within channel 48 and in contact with base 44. Lips 50 thereby restrict compressor 40 to lateral motions within channel 48. Ledges 70 are formed in side walls 52 of compressor 40 to underlie lips 50 and guide the lateral movement of compressor 40 within channel 48. Interior end portion 53 of each lip 50 defines a shoulder 55 over which a latch 56 on compressor 40 is received to lock compressor 40 in place following compression of IOL 12 for "single-use" of packaging system 10. Optionally, an additional abutting flange (not shown) or like construction may also be included in the construction of compressor 40 and compression chamber 26 to prevent compressor 40 from being removed from channel 48 once fully inserted.

Compressor 40 preferably includes side walls 52 with ledges 70 adapted to be matingly received within channel 48, and an interior wall 62 adapted to engage and compress IOL 12. A cover flange 64 projects beyond interior wall 62 to overlie interior surface 58 of base 44 in support 30. Cover flange 64 also encloses opening 38 when compressor 40 is moved within channel 48. Latches 56 are positioned along each side wall 52 of compressor 40 above cover flange 64. Latches 56 have ramps 65 that ease the inward movement of compressor 40, and abutting faces 68 that protrude out to engage shoulders 55 to lock compressor 40 in its closed position within support 30.

Additive plunger 72 extends through opening passage 74 in end wall 76 of compressor 40, which is adapted to receive additive plunger 72. Additive plunger 72 includes a base 78 and a body 80 matingly received within compressor 40 to contact and push additive material 13 from reservoir 60 and into compression chamber 26. Reservoir 60 is formed in the interior 90 of compressor 40 defined by side walls 52, interior wall 62, exterior wall 92, base wall 94 and end wall 76. Upon movement of additive plunger 72 into interior 90 of compressor 40, additive material 13 in reservoir 60 is dispelled through ports 82 into compression chamber 26 prior to compression of IOL 12 with interior wall 62 of compressor 40.

Compressor 40 is laterally movable between an open position wherein cover flange 64 does not cover interior surface 58 of support 30 as illustrated in FIG. 1, and a closed position wherein cover flange 64 overlies interior surface 58 and latches 56 engage shoulders 55. When latches 56 engage shoulders 55, free edge 96 of compressor 40 abuts chamber edge 98 of compression chamber 26. A void 66 in compression chamber 26 is defined by interior surface 58, chamber wall 100 and interior wall 62. Void 66 lies in fluid communication with open passage 18. Preferably an IOL 12 is packaged within void 66 in proper orientation for implantation within an eye. IOL 12 is packaged within void 66 by non-permanently sealing IOL 12 within void 66 as illustrated in FIG. 1. IOL 12 is preferably non-permanently sealed within void 66 using a suitable preferably transparent cover 84 such as but not limited to a heat sealed polymer film or a friction fit "snap-open" synthetic material cap. Other methods of non-permanently sealing IOL 12 within void 66 could likewise be implemented. Cover 84 functions to maintain the orientation of IOL 12 and to protect IOL 12 from damage during sterilization by methods known to those skilled in the art, shipping and storage. Cover 84 is preferably transparent to allow for visual inspection of IOL 12 prior to removal of cover 84 by medical personnel at the time of surgery. Preferably, in addition to non-permanently sealing IOL 12, cover 84 likewise non-permanently seals ports 82 in interior wall 62 of compressor 40 until removal of cover 84. Alternatively, rather than having one cover 84 non-permanently sealing both IOL 12 and ports 82, IOL 12 and ports 82 may each be non-permanently sealed with individual covers 84. Upon removal of preferably the one cover 84 by applying force to extended edge 86 of cover 84 extending beyond free edge 96 of compressor 40, additive material 13 in reservoir 60 may be dispelled into compression chamber 26 and onto IOL 12. Additive material 13 is dispelled from reservoir 60 by movement of additive plunger 72 within interior 90 of compressor 40. The movement of additive plunger 72 within interior 90 compresses film additive container 102 against one or more spikes 101 of interior wall 62 to pierce film additive container 102. Upon piercing film additive container 102, additive material 13 flows through ports 82 and onto IOL 12. Additive material 13 may be a viscoelastic material, a lubricant, an anti-inflammatory agent, an antibiotic, an anti-microbial agent or a combination thereof.

Once additive material 13 is dispersed onto IOL 12, IOL 12 is compressed. Upon movement of compressor 40 within channel 48, interior wall 62 and chamber wall 100 receive and hold a peripheral edge 104 of optic portion 14 to prevent the peripheral edge 104 from being folded over optic portion 14 or turning when compressor 40 is moved into its fully closed and locked position. More specifically, peripheral edge 104 of optic 14 is oriented generally along a central plane parallel to interior surface 58 and cover flange 64.

Retainers 106 function to hold and support optic portion 14 of IOL 12 in this generally planar relationship during compression of optic portion 14. Since peripheral edge 104 of optic portion 14 is not folded over optic portion 14, the lens expands laterally within the eye without a swinging motion. This lateral shifting of peripheral edge 104 for expansion of optic portion 14 is safer and less likely to contact and damage tissues within an eye than if a swinging motion were necessary to unfold optic portion 14. In the preferred construction, retainers 106 are formed as opposed non-parallel walls 108. Retainers 106 could have one of any number of geometric profiles so long as retainers 106 maintain peripheral edge 104 of optic portion 14 in a substantially planar orientation and permit advancement of IOL 12 into an eye.

Figure 2:
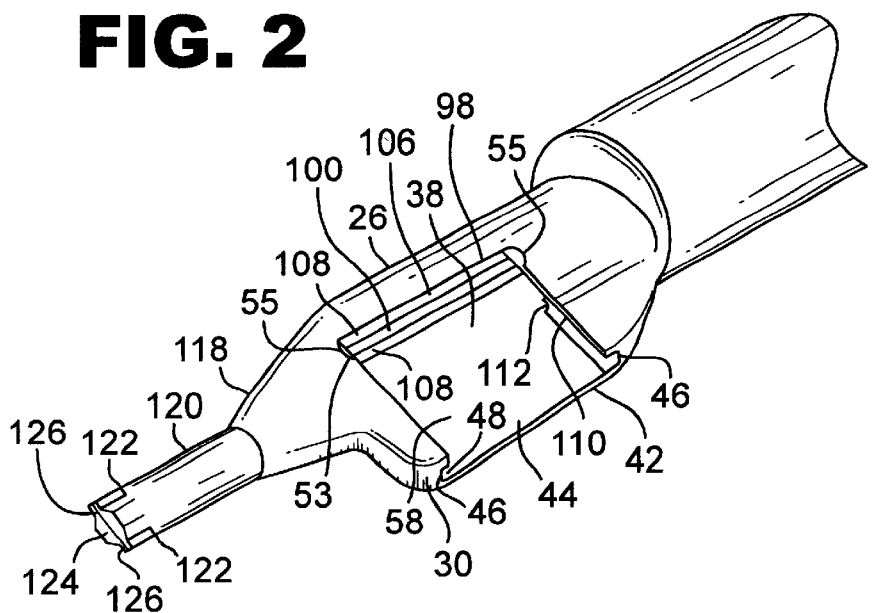
FIG. 2 is a partial perspective view of the packaging system of FIG. 1 with the compressor and additive plunger removed.
Figure 3:
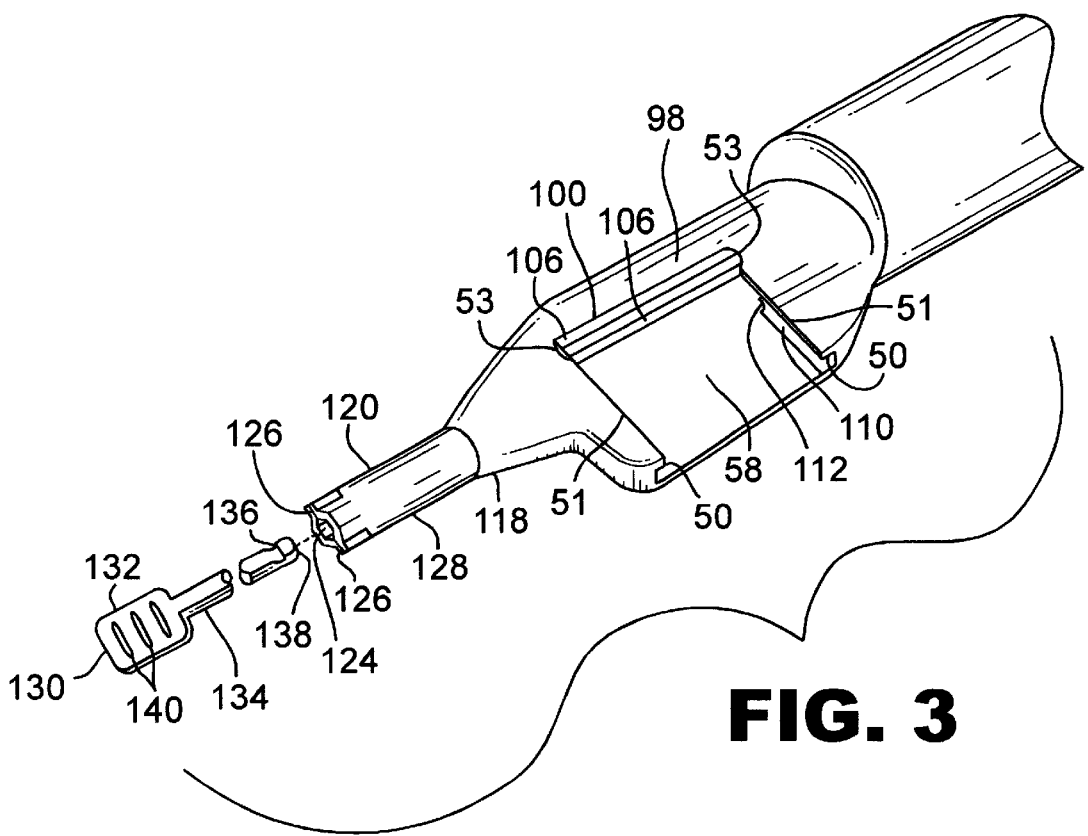
FIG. 3 is a partial perspective view of the packaging system of FIG. 1 with the compressor and additive plunger removed and an exploded haptic guide.
Figure 4:
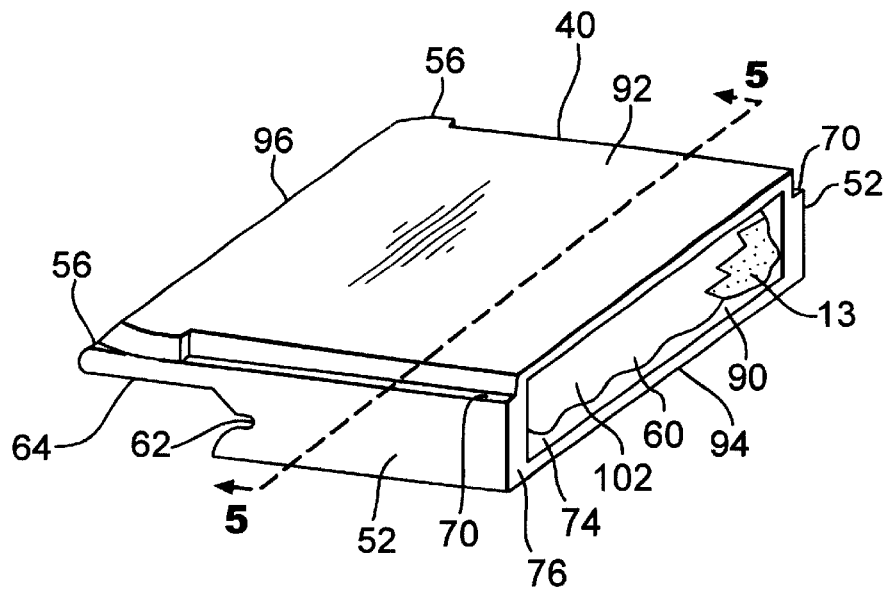
FIG. 4 is a perspective view of the compressor of FIG. 1.
Figure 5:
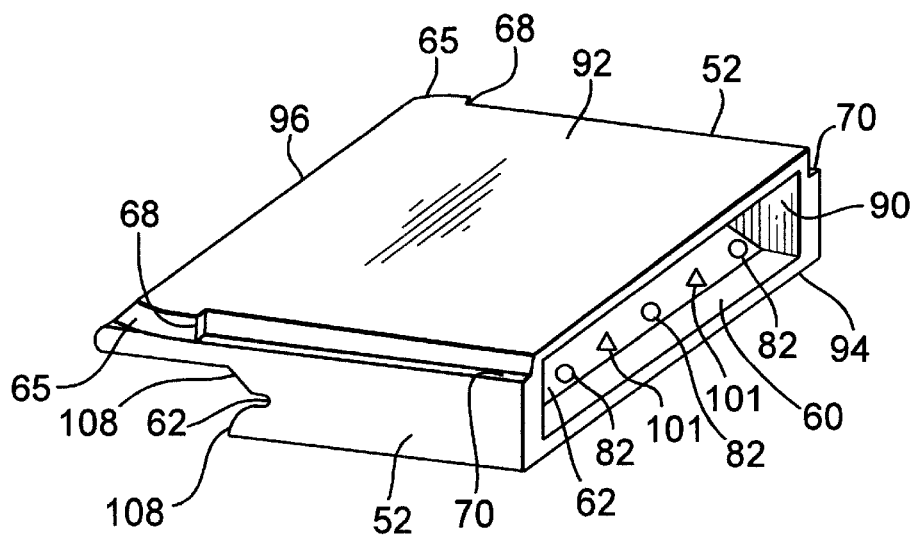
FIG. 5 is a cross sectional perspective view of the compressor of FIG. 4 taken along line 5—5.
Figure 6A:
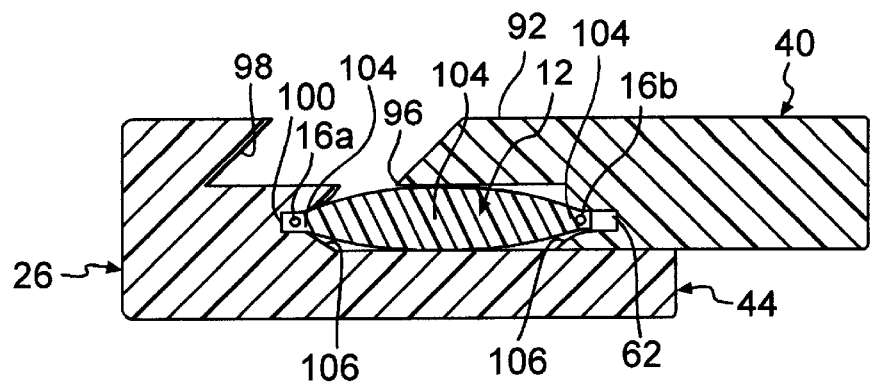
FIGS. 6A–6C are cross-sectional views of the packaging system of FIG. 1 taken along line 6—6 with the compressor at different stages of compression of an intraocular lens.
Figure 6B:
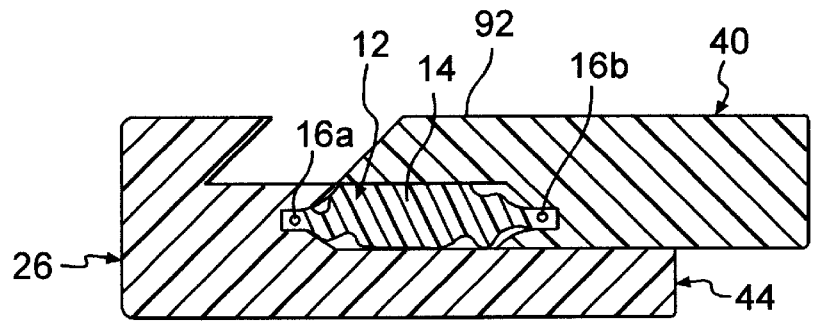
Figure 6C:
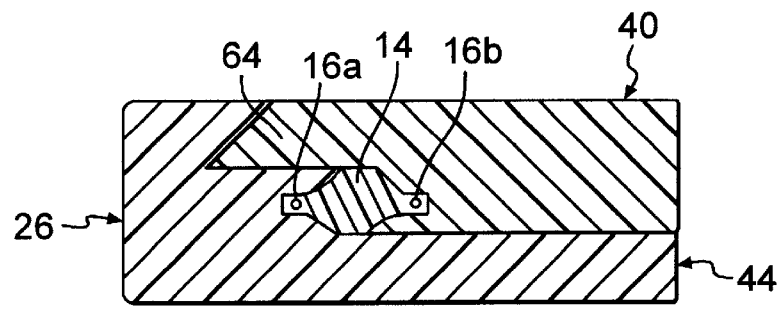

Compressor 40, when in its fully closed and locked position, partially defines void 66. Void 66 is defined by interior wall 62 with retainers 106, interior surface 58, chamber wall 100 with retainers 106, and cover flange 64. Void 66 is in fluid communication with open passage 18 through which IOL 12 is advanced by tip 36 of plunger 32. In moving compressor 40 into a fully closed and locked position, interior wall 62 is advanced within channel 48. Peripheral edge 104 of optic portion 14 is received by interior wall 62 and chamber wall 100 as illustrated in FIG. 6A. Continuing advancement of compressor 40 causes peripheral edge 104 to be snugly pushed into direct contact with interior wall 62 and chamber wall 100 between retainers 106 in order to prevent release as illustrated in FIG. 6B. This movement of compressor 40 also begins to laterally compress optic portion 14. Although optic portion 14 will have a tendency to crumple slightly during compression, peripheral edge 104 of optic portion 14 is retained in a generally planar relationship by retainers 106. Finally, when latches 56 are locked on shoulders 55, IOL 12 is in a compressed configuration between interior wall 62 and chamber wall 100 as illustrated in FIG. 6C. Interior surfaces 110 of alignment arms 46, illustrated in FIGS. 2 and 3, are formed with a profile edge 112 identical to that of interior wall 62 to form continuous open passage 18.

Figure 6D:
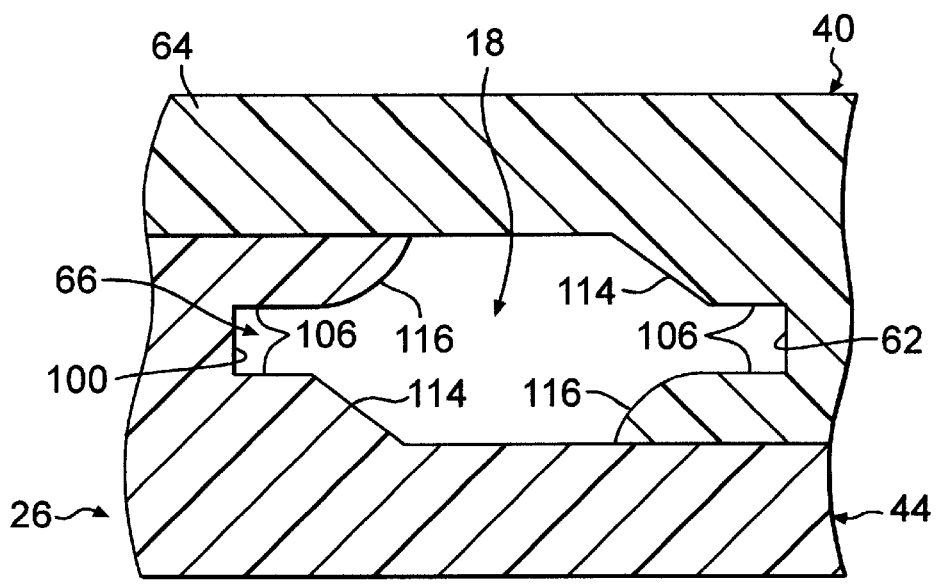
FIG. 6D is a partial cross-sectional view of the packaging system of FIG. 1 taken along line 6—6 with the compressor in a closed position and the intraocular lens omitted.

While non-parallel walls 108 of retainers 106 can be identical, mirror images of one another, non-parallel walls 108 are preferably asymmetrical, as illustrated in FIG. 6D, to better orient haptic elements 16 for insertion. More specifically, interior wall 62 and chamber wall 100 are each partially defined by non-parallel walls 108. One non-parallel wall 108 of each interior wall 62 and chamber wall 100 may have a more linear profile 114 than its opposing non-parallel wall 108 that may have a more curved profile 116.

As compressor 40 is moved within channel 48, peripheral edge 104 of optic 14 is received into interior wall 62 and chamber wall 100 as illustrated in FIGS. 6A–6D. As IOL 12 is compressed, non-parallel walls 108 cause the IOL 12 to dip slightly about the more linear profile 114 non-parallel wall 108 and create a slight twist in optic 14 so that leading haptic 16a tends to point in a downward direction. This downward orientation of leading haptic 16a will enable the surgeon to more easily place haptic 16a within the capsule of an eye. Similarly, trailing haptic 16b is shifted to incline slightly upward to avoid contact by tip 36 of plunger 32 to enable tip 36 to directly engage peripheral edge 104 of optic 14.

Cannula 28 is in fluid communication with compression chamber 26 through open passage 18. Cannula 28 preferably includes a proximal, funnel-shaped portion 118 which tapers to further compress IOL 12, and an elongate distal portion 120 which directs compressed IOL 12 into an eye.

Nevertheless, cannula 28 could be formed to have a uniform taper across its length or provided with no taper if, for example, compressor 40 has a longer stroke to complete the desired compression of IOL 12.

Figure 7:
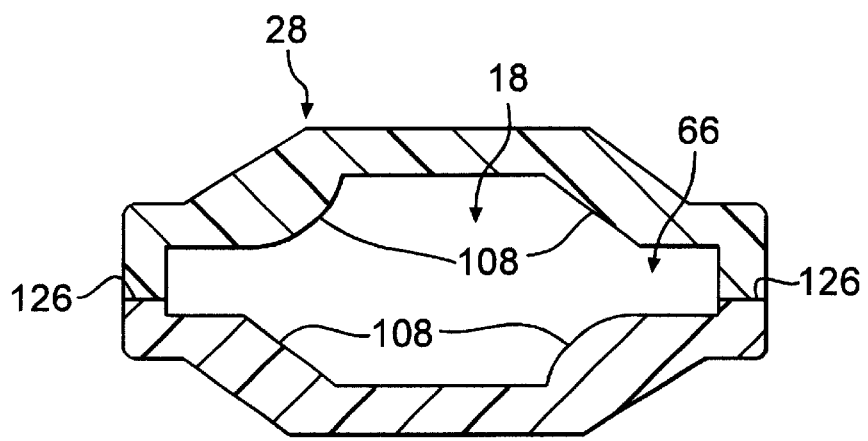
FIG. 7 is a cross-sectional view of the packaging system of FIG. 1 taken along line 7—7.

Open passage 18 which extends through cannula 28 and compression chamber 26 forms a continuous duct through which IOL 12 is moved (FIG. 7). Within cannula 28, open passage 18 is defined by cannula interior surface 122 shaped to match interior wall 62 and chamber wall 100 of compression chamber 26 to maintain continuous retention of peripheral edge 104 as IOL 12 is advanced into an eye. Interior surface 122 of cannula 28 preferably converges at an angle of about 7 degrees to further compress IOL 12 as it is advanced through cannula 28. As noted above, interior surface 122 of cannula 28 continues to hold peripheral edge 104 of optic 14 as IOL 12 passes through cannula 28 to maintain the generally planar orientation of peripheral edge 104. This planar orientation of peripheral edge 104 prevents turning or rotation of IOL 12 during its advancement though cannula 28.

Open tip 124 of cannula 28 is an elongate, slender tube to permit entry of packaging system 10 through a relatively small incision of approximately 3.5 mm or less (not shown). Open tip 124 of cannula 28 is preferably provided with a pair of opposed longitudinal slits 126 as illustrated in FIGS. 1–3. Slits 126 are wide enough to permit peripheral edge 104 of optic 14 to extend outward beyond the exterior surface 128 of cannula 28. Slits 126 therefore permit lateral expansion of IOL 12 prior to release into an eye. As a result, the natural resilient force that biases IOL 12 to assume its original uncompressed shape is dissipated in the controlled environment of cannula 28. IOL 12 is thus not released with any velocity as in many prior art inserters. Further, since IOL 12 is compressed without folding peripheral edge 104 over optic 14, expansion of IOL 12 requires only an outward, lateral movement of optic 14. IOL 12 experiences no swinging of optic 14 or haptic elements 16 within the eye which risks damaging the interior of the eye. Slits 126 also continue to hold optic 14 and prevent turning or rotation of IOL 12 so implantation of IOL 12 in its proper orientation is ensured. Accordingly, insertion of IOL 12 with packaging system 10 provides a safer implantation procedure than heretofore realized.

Haptic guide 130 as illustrated in FIG. 3 is optionally provided cannula 28 of packaging system 10 to ensure the proper positioning of leading haptic 16a. Haptic guide 130 includes a generally flat pull-tab 132 and a slender rod 134 projecting from pull-tab 132. Rod 134 is sized to be received within open tip 124 of cannula 28. Hook 136 or other shoulder element is formed on free end 138 of rod 134. In use, rod 134 is fully inserted into open tip 124 and open passage 18 so that hook 136 is visible through opening 38 in compression chamber 26. IOL 12 is loaded within void 66 by the manufacturer with leading haptic 16a looped over hook 136. Pull-tab 132 is manually pulled to remove rod 134 from packaging system 10. Removal of haptic guide 130 can be performed before or after closure of compressor 40. As rod 134 is removed from packaging 10, hook 136 engages and pulls leading haptic 16a so that it is positioned within open passage 18 within cannula 28. This positioning of leading haptic 16a tends to non-permanently partially straighten haptic 16a within open passage 18. This non-permanent partial straightening of leading haptic 16a reduces the risk of leading haptic 16 becoming stuck in open passage 18 and lodging around optic 14 during insertion. Ribs 140 or the like are preferably formed on pull-tab 132 to enhance the manual grasping of pull-tab 132.

The above detailed description discloses the preferred embodiments of the present invention. Various other embodiments as well as many changes and alterations may be made without departing from the spirit and broader aspects of the invention as defined in the claims. For example, the compression chamber, with or without the cannula, can be formed as a separable packaging system for compressing the lens. The packaging system could then be placed within an injector device for insertion of the lens into an eye after the lens has been compressed. Also, optic 14 could be manipulated into a U-shape, W-shape, or other folded configuration as opposed to direct compression as described. So long as peripheral edge 104 of optic 14 is maintained in a generally planar orientation within side wall 62 and chamber wall 100, IOL 12 will still expand with a lateral shifting motion to avoid the broad swinging open of peripheral edge 104 and haptic elements 16 within an eye.

I claim:

1. A packaging system for an intraocular lens and optionally an additive material capable of use as a surgical inserter comprising:

a tubular member defining a passage with a plunger adapted to receive and direct an intraocular lens into an eye, a compressor with an optional reservoir space formed therein movably attached to said tubular member for laterally compressing said intraocular lens within said passage, an optional additive material plunger movably attached to said compressor for elimination of said optional reservoir space, one or more transparent covers for non-permanently sealing said intraocular lens within said passage and an optional additive material within said optional reservoir space prior to use, and retainers in said passage for maintaining a peripheral optic edge of the intraocular lens in a generally planar relationship during compression.

2. A packaging system for an intraocular lens and an additive material capable of use as a surgical inserter comprising:

a tubular member defining a passage with a plunger adapted to receive and direct an intraocular lens into an eye, a compressor formed with a reservoir space therein movably attached to said tubular member for laterally compressing said intraocular lens within said passage, an additive material plunger movably attached to said compressor for elimination of said reservoir space, one or more transparent covers for non-permanently sealing said intraocular lens within said passage and an additive material within said reservoir space prior to use, and retainers in said passage for maintaining a peripheral optic edge of said intraocular lens in a generally planar relationship during compression.

3. The packaging system of claim 1 or 2 wherein said plunger is movably received in said passage for advancing the intraocular lens through said passage and expelling the intraocular lens within an eye.

4. The packaging system of claim 1 or 2 wherein said compressor defines a sidewall portion.

5. The packaging system of claim 1 or 2 wherein said retainers each include two non-parallel walls.

6. The packaging system of claim 1 or 2 wherein said retainers each include two non-parallel walls, one of which has a more linear profile and the other a more curved profile.

7. The packaging system of claim 1 or 2 wherein said retainers extend longitudinally substantially the entire passage to prevent uncontrolled turning of said intraocular lens during advancement through said passage.

8. The packaging system of claim 1 or 2 wherein a distal end of said tubular member is provided with opposed slits through which said intraocular lens can expand prior to discharge from said passage.

9. The packaging system of claim 1 or 2 wherein said tubular member includes a guideway for directing the movement of said compressor.

10. The packaging system of claim 1 or 2 wherein said tubular member includes an opening for positioning said intraocular lens within said passage, and said compressor includes a flange which closes said opening as said intraocular lens is compressed.

11. The packaging system of claim 1 or 2 wherein said additive material is one or more materials selected from the group consisting of viscoelastics, lubricants, anti-inflammatory agents, antibiotics and anti-microbial agents.

12. The packaging system of claim 1 or 2 wherein said intraocular lens is formed with an optic, a leading haptic and a trailing haptic, and said packaging system further includes a haptic guide received within said passage to engage and non-permanently partially straighten said leading haptic in the direction of advancement of said intraocular lens.

13. The packaging system of claim 1 or 2 wherein said intraocular lens is formed with an optic, a leading haptic and a trailing haptic, and said packaging system further includes a haptic guide received within said passage formed of a rod with a free end and a hook at said free end to engage and pull said leading haptic in said passage.

14. The packaging system of claim 1 or 2 wherein said intraocular lens is formed with an optic, a leading haptic and a trailing haptic, and said packaging system further includes a haptic guide received within said passage formed of a rod with a free end, a hook at said free end to engage and pull said leading haptic in said passage and a pull-tab for manual grasping and pulling of said haptic guide out of said passage.

15. A method for implanting an intraocular lens and optionally an additive material into an eye through an incision using the packaging system of claim 1 comprising:

removing said one or more transparent covers from said packaging system, dispelling said optional additive material from said optional reservoir space in said compressor and onto said intraocular lens, moving said compressor into said tubular member to compress said intraocular lens, and moving said plunger within said tubular member to expel said intraocular lens from said packaging system.

16. A method for implanting an intraocular lens and an additive material into an eye through an incision using the packaging system of claim 2 comprising:

removing said one or more transparent covers from said packaging system, dispelling said additive material from said reservoir space in said compressor and onto said intraocular lens, moving said compressor into said tubular member to compress said intraocular lens, and moving said plunger within said tubular member to expel said intraocular lens from said packaging system.

17. The method of claim 15 or 16 wherein a distal end of said tubular member is provided with opposed slits through which said intraocular lens can expand prior to discharge from said passage.

18. The method of claim 15 or 16 wherein said tubular member includes a guideway for directing the movement of said compressor.

19. The method of claim 15 or 16 wherein said tubular member includes an opening for positioning said intraocular lens within said passage, and said compressor includes a flange which closes said opening as said intraocular lens is compressed.

20. The method of claim 15 or 16 wherein said additive material is one or more materials selected from the group consisting of viscoelastics, lubricants, anti-inflammatory agents, antibiotics and anti-microbial agents.

21. The method of claim 15 or 16 wherein said intraocular lens is formed with an optic, a leading haptic and a trailing haptic, and said packaging system further includes a haptic guide received within said passage to engage and non-permanently partially straighten said leading haptic in the direction of advancement of said intraocular lens.

22. The method of claim 15 or 16 wherein said intraocular lens is formed with an optic, a leading haptic and a trailing haptic, and said packaging system further includes a haptic guide received within said passage formed of a rod with a free end and a hook at said free end to engage and pull said leading haptic in said passage.

23. The method of claim 15 or 16 wherein said intraocular lens is formed with an optic, a leading haptic and a trailing haptic, and said packaging system further includes a haptic guide received within said passage formed of a rod with a free end, a hook at said free end to engage and pull said leading haptic in said passage and a pull-tab for manual grasping and pulling of said haptic guide out of said passage.

* * * * *